(12) United States Patent
Wolf et al.

(10) Patent No.: US 7,122,379 B2
(45) Date of Patent: Oct. 17, 2006

(54) DETERMINING THE REACTION PROGRESS OF GRAFT POLYMERIZATION REACTIONS

(75) Inventors: Udo Wolf, Kempen (DE); Ralf-Jürgen Born, Langenfeld (DE); Vera Buchholz, Köln (DE); Herbert Eichenauer, Dormagen (DE); Eckhard Wenz, Köln (DE); Wilhelm Bergmeier, Meerbusch (DE); Christof Boden, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 419 days.

(21) Appl. No.: 10/281,597

(22) Filed: Oct. 28, 2002

(65) Prior Publication Data

US 2003/0119199 A1    Jun. 26, 2003

(30) Foreign Application Priority Data

Oct. 30, 2001   (DE) ................................ 101 53 536
Feb. 4, 2002    (DE) ................................ 102 04 392

(51) Int. Cl.
*G01N 24/00*  (2006.01)
*G01N 33/44*  (2006.01)

(52) U.S. Cl. ........................... 436/173; 436/85; 436/34
(58) Field of Classification Search .................. 436/34, 436/85, 164, 166
See application file for complete search history.

(56) References Cited

U.S. PATENT DOCUMENTS 4,125,534 A   11/1978  Yee ............................ 260/315
4,661,383 A   4/1987   Elsenbaumer et al. ...... 427/302
6,072,576 A   6/2000   McDonald et al. ......... 356/300

FOREIGN PATENT DOCUMENTS

WO       98/08066    2/1998
WO       01/09201    2/2001

OTHER PUBLICATIONS

"Internal Standards" http://www.chemistry.adelaide.edu.au/external/soc-rel/content/int-std.htm, Sep. 2003.*
Wang et al. "Use of water as an internal standard in the direct monitoring of emulsion polymerization by fiber-optic Raman spectroscopy", Applied Spectroscopy, 1993, v. 47, No. 7, pp. 928-932.*
Schlenoff et al. "In-situ monitoring of emulsion and bulk polymerization by fiber optic Raman spectroscopy", Polymeric Materials Science and Engineering, 1995, v. 72, pp. 52-53.*
Al-Khanbashi et al. "Application of in-line fiber-optic Raman spectroscopy to monitoring emulsion polymerization reaction", Applied Spectroscopy Reviews, 1998, v. 33, No. 1&2, pp. 116-131.*

(Continued)

*Primary Examiner*—Yelena G. Gakh
(74) *Attorney, Agent, or Firm*—Nicanor A. Kohnoke

(57) ABSTRACT

A method of using Raman Spectra for determining the progress of a graft polymerization reaction is disclosed. The method entails (a) measuring at the beginning of the reaction and at a plurality of time intervals in the course of the reaction, continuously and on-site, the Raman spectrum in the wave number range of 100 to 4000 cm$^{-1}$ of one or more of the monomers and/or polymers entailed in the reaction and of at least one internal standard and (b) recording the spectra and (c) adding reaction partners necessary to the reaction continuously and/or discontinuously and (d) calculating the change in concentration of the monomers and polymers by comparing the spectra of the monomers or polymers with the internal standard.

11 Claims, 3 Drawing Sheets

OTHER PUBLICATIONS

Figure 1:
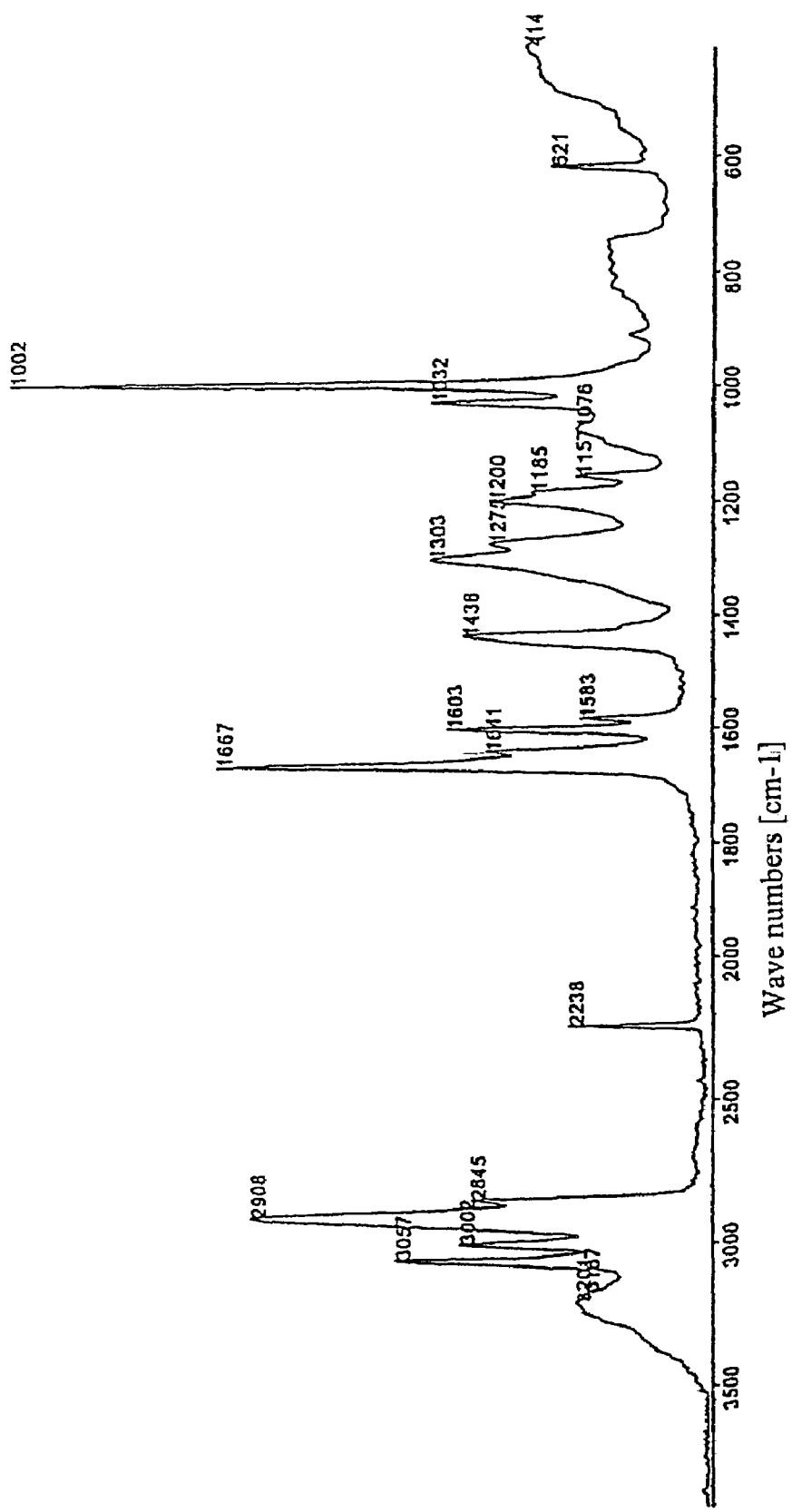

Van den Brink et al. "Emulsion (Co) polymerization of styrene and butyl acrylate monitored by on-line Raman spectroscopy", Macromolecular Symposia (2000), 150(Polymers in Dispersed Media), 121-126.*

Bauer et al. "On-line monitoring of a latex emulsion polymerization by fiber-optic FT-Raman spectroscopy. Part I: calibration", Applied Spectroscopy (2000), 54(4), 528-535.*

Van den Brink et al. "On-line monitoring and composition control of the emulsion copolymerization of VeoVA 9 and butyl acrylate by Raman spectroscopy", Polymer Reaction Engineering (2001), 9(2), 101-133.*

Fredericks et al. "Raman Mapping of plasma treated and grafted polymer surfaces" Proceedings of SPIE, Oct. 2001, v. 4469, pp. 1-8; Conference date Jul. 31, 2001.*

Journal of Applied Polymer Science, vol. 79, (date unavailable) 2001, pp. 426-436, Mark Van Den Brink et al, "Measurement of Partial Conversions During the Solution Copolymerization of Styrene and Butyl Acrylate Using On-Line Raman Spectroscopy".

* cited by examiner

DETERMINING THE REACTION PROGRESS OF GRAFT POLYMERIZATION REACTIONS

FIELD OF THE INVENTION

The invention relates to chemical reactions and more particularly to a method of using Raman spectroscopy in controlling graft polymerization reactions.

SUMMARY OF THE INVENTION

A method of using Raman Spectra for determining the progress of a graft polymerization reaction is disclosed. The method entails (a) measuring at the beginning of the reaction and at a plurality of time intervals in the course of the reaction, continuously and on-site, the Raman spectrum in the wave number range of 100 to 4000 $cm^{-1}$ of one or more of the monomers and/or polymers entailed in the reaction and of at least one internal standard and (b) recording the spectra and (c) adding reaction partners necessary to the reaction continuously and/or discontinuously and (d) calculating the change in concentration of the monomers and polymers by comparing the spectra of the monomers or polymers with the internal standard.

BACKGROUND OF THE INVENTION

Near-infrared Fourier transform Raman spectroscopy has been known in principle since it became commercially available in 1989, and it has developed into an efficient and routinely used spectroscopic method (J. Sawatzki, CLB Chemie in Labor und Biotechnik, Vol. 50, No. 9/1999). M. van den Brink, Journal of Applied Polymer Science, Vol. 79, 426–436 (2001) also reports on the measurement of the partial conversion of a copolymerization solution of styrene and butyl acrylate using online Raman spectroscopy. It has been established, however, that the calculation of individual monomer concentrations on the basis of individual vinyl peaks is not very suitable, since these bands overlap in the Raman spectrum.

WO 00/49395 concerns a process for the production of latex by emulsion (co)polymerization of at least one type of ethylenically unsaturated monomer, characterized in that the process is performed by continuous on-site control of the (co)polymerization, which comprises the following steps:

(i) an incident light ray, located in the spectral range between 200 nm and 1400 nm, preferably between 700 nm and 1400 nm, is transmitted into the emulsion
(ii) the light scattered by the reaction medium is detected and directed to a Raman spectrometer
(iii) the Raman spectrum, which represents the energy of the scattered light as a function of the wavelength shift relative to the incident light ray, is determined
(iv) the following values are calculated:
  a) either the intensities (areas or heights) of specific spectral lines of the free, non-(co)polymerized monomer(s) in the reaction mixture and of the polymer obtained
  b) or the concentrations of the free, non-(co)polymerized monomer(s) in the reaction medium and of the polymer obtained based on the Raman spectrum with the aid of quantitative spectral analysis methods, preferably with the aid of multivariate chemometric methods
(v) the process data is calculated from the concentrations of the free monomer(s) and of the polymer obtained or from the intensities (areas or heights) of the specific spectral lines of the free monomer(s) in the reaction medium and of the polymer obtained,
(vi) this process data is compared with the specific reference data for the process for producing latex with the specified properties
(vii) and the reaction parameters, such as temperature, pressure, stirring of the mixture and monomer supply, are controlled in such a way that the deviation between the process data measured online and the reference process data is minimized.

The details given in WO 00/49395 about the direct intensity measurement of the Raman lines illustrate the serious disadvantage that these cannot be accurately assigned to a defined (copolymerized) monomer. The specified multivariate chemometric methods are likewise often unsuitable for an industrial conversion since they involve a great deal of calibration work.

By contrast, the present invention concerns the means for determining the progress of graft polymerization reactions.

This is achieved by measuring the Raman spectrum at the beginning and at various intervals during the course of the reaction, characterized in that before the start of the reaction the Raman spectrum of one or more of the monomers and/or polymers to be analyzed and of at least one internal standard is recorded in the wave number range from 100 to 4000 $cm^{-1}$, reaction partners to perform the graft polymerization are added continuously and/or discontinuously and further Raman spectra are recorded in the wave number range from 100 to 4000 $cm^{-1}$ at intervals during the course of the reaction, and the change in concentration of the monomers and polymers is calculated from the spectra in consideration of the internal standard.

The length of the time intervals depends on the total reaction time and the reaction rates. Typically, a spectrum is recorded at intervals of 1 second to 30 minutes, preferably 10 seconds to 10 minutes.

As an exemplary embodiment of the process, the present process may be used for the controlled production of ABS by grafting of polybutadiene, whereby a known amount of polybutadlane $M_{PB}$ is placed in a reactor in the form of an emulsion, grafting is started at time t=0 and performed by known means by continuous addition and polymerization of the monomers styrene and aciylonitrile, and the Raman spectra (Iυ) are recorded at short intervals, preferably in the range 4000 to 100 $cm^{-1}$ (Stokes range), otherwise in the range –4000 to 4000 $cm^{31\ 1}$ (anti-Stokes and Stokes range). In contrast to the teaching from WO 00/49 395, palybutadiene is used according the invention as the internal standard for interpreting Raman spectra.

The majority of the Raman spectrometer systems that are commercially available today can be divided into two categories:

FT Raman Spectrometers:

The Raman spectrum is excited with the aid of a Nd:YAG laser ($\lambda$=1.06 μm). An interferometer with a near-infrared lens system is used to detect the Raman radiation. The non-wavelength shifted Raleigh radiation is suppressed with the aid of a Notch filter.

Since the intensity of the Raman radiation is proportional to $1/\lambda^4$, the relatively long-wave excitation using the Nd:YAG laser is initially unfavourable. However, since a Nd:YAG laser with relatively high power is available (typically a few watts) and moreover the disruptive fluorescence that is very common with excitation in the UV/VIS range does not occur, Raman spectra of organic substances can generally be recorded without any difficulty.

Dispersive Raman Spectrometers:

Different types of laser can be used to excite Raman radiation. The use of He:Ne lasers (λ=632 nm) and of semiconductor lasers (for example λ=785 nm) is conventional.

Spectral breakdown and detection are performed using a grid and a (thermoelectrically cooled) CCD detector. Raleigh scattered radiation is blocked with the aid of a Notch filter. Systems of this type can be used particularly easily in a multiplex operation, since multiple spectra can be mapped simultaneously onto the CCD junction-type detector and read out one after another.

Disruptive fluorescence is commonly observed with short-wave excitation. The fluorescence can completely obscure the Raman spectrum.

The absolute height of a Raman emission peak is not reproducible. According to the invention Raman spectra are therefore always interpreted using internal standards.

The spectral responsivity of different Raman spectrometers is not the same. Calibrations can therefore only be transferred between different spectrometers with reservations. The calibration factors should be checked and adjusted on transfer to another spectrometer.

Other influences on spectral responsivity can occur due to the medium to be analyzed itself, since this can absorb radiation. The Stokes-shifted Raman spectrum (fundamental vibration range) is in the range $\upsilon_0$ to $\upsilon_0$–4000 cm$^{-1}$, which in the case of excitation with the Nd:YAG laser means the range from 9400–5400 cm$^{-1}$. In this spectral range water exhibits a not insignificant absorption. In emulsion polymerization the effective path length of the Raman radiation in the sample can depend on the (variable) scattering properties of the emulsion. In this way the relative intensity ratios of the Raman spectrum also depend on the emulsion properties. This is especially true for the range $\upsilon > 2000$ cm$^{-1}$ of the Raman spectrum when excitation is by means of the Nd:YAG laser.

In the case of excitation with the 785 nm semiconductor laser, the Raman radiation (fundamental vibrations) is in the range from 12700 to 8700 cm$^{-1}$. In this spectral range the self-absorption of the medium to be analyzed (for example water) is generally markedly weaker. The influence of the emulsion properties on the Raman spectrum is correspondingly lower.

The laser radiation used to excite the Raman spectrum can be polarized or unpolarized. A polarizer can optionally be used on the detection side to exclude possibly undesirable polarizing directions. There can be an angle of between 0 and 360°, preferably 90 to 180°, between the exciting laser beam and the detection lens.

Raman spectra can preferably be recorded using an optical fibre coupling. Using an optical probe (for example a Raman measuring head supplied by Bruker, Karlsruhe), the Raman spectra of the contents of a reactor can be obtained by means of a sight glass fitted to the reactor. Immersion probes, which are in direct contact with the product to be analyzed and are connected to a Raman spectrometer by means of optical fibres, are also available.

The data can be recorded offline, online or inline. In the context of the present invention offline means that an aliquot of the reaction mixture is removed and measured in a separate area. Online denotes a procedure whereby a part of the reaction mixture is diverted from the reaction vessel through a loop, for example, measured and then returned to the reaction mixture. Inline means that the measurement is performed directly in the reaction vessel. In the context of the present invention the data is preferably recorded online or inline, particularly preferably inline.

In the simplest instance of a batchwise emulsion polymerization, a monomer that is poorly soluble in water, for example styrene, is typically polymerized in water as dispersive medium in the presence of an emulsifier (for example a fatty soap or an alkane sulfonate having at least 12 carbon atoms in the chain) and a radical former (for example potassium peroxodisulfate) at temperatures from 55 to 85° C. with stirring.

Even in this simplest instance a distinction is made as follows:

a) Phase I, latex particle formation (latex particle nucleation). This lasts until the emulsifier has been largely absorbed at the growing latex particle/water or monomer particle/water interface.

b) Phase II, particle growth. Virtually no more new latex particles are formed; in addition to monomer droplets there are also monomer-swollen latex particles in which the polymerization reaction takes place. Once the monomer droplets have disappeared, c) Phase III sees the removal by polymerization of the monomer incorporated into the latex particles by swelling. Whereas in Phase I and Phase II the latex particles are swollen with monomer to the maximum possible degree, in Phase III, starting from the maximum swelling, the monomer concentration in the latex particles falls steadily.

The kinetics of the emulsion polymerization, which takes place almost exclusively in the latex particles in the case of monomers that are poorly soluble in water, is determined by the monomer concentration and the radical concentration in the latex particles and by the number of latex particles per unit volume of emulsion. The rate of chain growth in the macromolecules is dictated by the temperature-related specific propagation constant $k_p$ of the monomer in question.

In principle many emulsion polymerizations are performed not batchwise but semicontinuously because of the input of heat and out of safety considerations. The monomers are added so quickly that the liberated heat of polymerization can be eliminated effectively if cooling facilities are provided.

In most cases Phase I of the emulsion polymerization is also deliberately avoided by the use of a seed latex (introduction of monomer into the prepared seed latex).

In semicontinuous seeded emulsion polymerization with monomer introduction, a condition from Phase III can be identified at a specific monomer conversion (starved polymerization).

It is precisely at this point that the introduction of monomer can start to be controlled according to an online measurement of the monomer concentration. The rate of addition of the monomer is controlled on the basis of the monomer concentration measured online. If the monomer concentration drops, the introduction rate is increased; if it rises, the monomer introduction is reduced. In this way the stationary conversion in the latex particles can be kept constant at a desired level over an extended period of the emulsion polymerization.

In acrylonitrile/butadiene copolymerization, for example, the relative proportions of monomers and the amounts of copolymer in the copolymer produced can be detected online. In butadiene emulsion polymerization, for example, once the monomer droplets have disappeared the butadiene/polybutadiene ratio can be determined online very accurately. If the quantity of butadiene added is known, the conversion is therefore also known.

The process according to the invention can particularly preferably be used for the controlled production of graft polymers by grafting monomers onto a graft base (GB), whereby a known amount of graft base $M_{GB}$, in the form of an emulsion for example, is placed in a reactor, grafting is started at time t=0 and performed by known means by continuous addition and polymerization of the monomer(s), and the Raman spectra I($\upsilon$) are recorded at short intervals, preferably in the range 4000 to 100 cm$^{-1}$ (Stokes range), otherwise in the range −4000 to 4000 cm$^{-1}$ (anti-Stokes and Stokes range).

The Raman spectra for individual components often overlap. Conventional chemometric methods for interpreting the spectra, with the aid of which overlapping structures can be made accessible in order to determine the concentrations quantitatively, are scarcely suitable as interpretation methods since the calibration involves providing emulsions of defined concentrations and varying all of the individual components, which is extremely complex. The interpretation of the spectra according to the invention is therefore performed using an automated spectral interpretation program.

In the case of a typical graft copolymerization of two monomers (MO1, MO2) onto a graft base (GB), in addition to these starting components the homopolymers of MO1 and MO2 (PO1 and PO2, respectively) are also detected and used for the evaluation.

The calibration factors (K); KPO1, KPO2, KMO1, and KMO2 are preferably first determined in a calibration step, using the calculations infra, from the Raman spectra IGB($\upsilon$) of the graft base (GB), IPO1($\upsilon$) and IPO2($\upsilon$) of the homopolymers PO1 and PO2, IMO1($\upsilon$) and IMO2($\upsilon$) of the monomers MO1 and MO2, which have previously been measured and stored in digitized form in an EDP unit, and the current spectrum I($\upsilon$) of the reactor contents, at $\upsilon$min=−4000 cm-1 (anti-Stokes range) and $\upsilon$max=4000 cm-1 (Stokes range), preferably $\upsilon$min=100 cm-1 and $\upsilon$max=4000 cm-1, particularly preferably $\upsilon$min=500 cm-1 and $\upsilon$max=2500 cm-1, most particularly preferably $\upsilon$min=750 cm-1 and $\upsilon$max=1800 cm-1, whereby the Raman spectra IK($\upsilon$) for mixtures with known proportions are recorded and the factors fi are calculated using the condition:

$$\sum_{\upsilon_{min}}^{\upsilon_{max}} \{I_k(\upsilon) - [f_{GB} * I_{GB}(\upsilon) + f_{PO1} * I_{PO1}(\upsilon) + f_{PO2} * I_{PO2}(\upsilon) + f_{MO1} * I_{MO1}(\upsilon) + f_{MO2} * I_{MO2}(\upsilon) + f_k]\}^2 = \text{minimum}$$

from which are calculated the quotients $$Q_{PO1} = f_{PO1}/f_{GB}$$

$$Q_{PO2} = f_{PO2}/f_{GB}$$

$$Q_{MO1} = f_{MO1}/f_{GB}$$

$$Q_{MO2} = f_{MO2}/f_{GB}$$

and the parts by weight W with the known quantities M:

$$W_{PO1} = M_{PO1}/M_{GB}$$

$$W_{PO2} = M_{PO2}/M_{GB}$$

$$W_{MO1} = M_{MO1}/M_{GB}$$

$$W_{MO2} = M_{MO2}/M_{GB}$$

and the calibration factors K are calculated from the following equations, which in each case can be employed for the Raman spectra of calibration samples which have a high proportion of those components, the calibration factor of which can be determined:

$$K_{PO1} = W_{PO1}/Q_{PO1}$$

$$K_{PO2} = W_{PO2}/Q_{PO2}$$

$$K_{MO1} = W_{MO1}/Q_{MO1}$$

$$K_{MO2} = W_{MO2}/Q_{MO2}$$

Calibration samples for determining the calibration factors $K_{MO1}$ and $K_{MO2}$ can be produced, for example, by adding monomers $M_{O1}$ or $M_{O2}$ in defined quantities to a defined quantity of polybutadiene latex and a defined polybutadiene content. In order to determine the calibration factors $K_{PO1}$ and $K_{PO2}$, copolymer suspensions with varying, known proportions of copolymer can be used, for example.

During the graft polymerization the factors $f_i$ are calculated from the current spectrum I($\upsilon$) of the reactor content and the condition $$\sum_{\upsilon_{min}}^{\upsilon_{max}} \{I(\upsilon) - [f_{GB} * I_{GB}(\upsilon) + f_{PO1} * I_{PO1}(\upsilon) + f_{PO2} * I_{PO2}(\upsilon) + f_{MO1} * I_{MO1}(\upsilon) + f_{MO2} * I_{MO2}(\upsilon) + f_k]\}^2 = \text{minimum}$$

(weighted subtraction), whereby the addition is performed across all data points of the spectra $I_i(\upsilon)$ which are digitized in the same form.

From these the quotients $$Q_{PO1} = f_{PO1}/f_{GB}$$

$$Q_{PO2} = f_{PO2}/f_{GB}$$

$$Q_{MO1} = f_{MO1}/f_{GB}$$

$$Q_{MO2} = f_{MO2}/f_{GB}$$

and, using the calibration factors K, the proportions W of:

Polymer1 to graft base: $W_{PO1} = K_{PO1} * Q_{PO1}$

Polymer2 to graft base: $W_{PO2} = K_{PO2} * Q_{PO2}$

Monomer1 to graft base: $W_{MO1} = K_{MO1} * Q_{MO1}$

Monomer2 to graft base: $W_{MO2} = K_{MO2} * Q_{ACN}$ are calculated, from which using:

$$M_{PO1} = W_{PO1} * M_{GB}$$

$$M_{PO2} = W_{PO2} * M_{GB}$$

$$M_{MO1} = W_{MO1} * M_{GB}$$

$$M_{MO2} = W_{MO2} * M_{GB}$$

the absolute quantities of polymer1 $M_{PO1}$, polymer2 $M_{PO2}$, monomer1 $M_{MO1}$ and monomer2 $M_{MO2}$ in the reactor are calculated, these are compared with the required concentrations after a time $\Delta t$ from the start of polymerization and the current quantities are adjusted to the required quantities for the reaction at time $t_0+\Delta t$ by varying the quantities of monomer1 and/or monomer2 that are added or by increasing or reducing the polymerization rates.

Graft polymers in the sense of the present invention include, for example:

A.1 5 to 95, preferably 30 to 90 wt. % of at least one vinyl monomer on

A.2 95 to 5, preferably 70 to 10 wt. % of one or more graft bases having glass transition temperatures <10° C., preferably <0° C., particularly preferably <−20° C.

Monomers A.1 are preferably mixtures of

A.1.1 50 to 99 parts by weight of vinyl aromatics and/or vinyl aromatics substituted in the ring (such as e.g. styrene, α-methyl styrene, p-methyl styrene, p-chlorostyrene) and/or methacrylic acid ($C_1$–$C_8$) alkyl esters (such as methyl methacrylate, ethyl methacrylate) and A.1.2 1 to 50 parts by weight of vinyl cyanides (unsaturated nitriles such as acrylonitrile and methacrylonitrile) and/or (meth)acrylic acid ($C_1$–$C_8$) alkyl esters (such as methyl methacrylate, n-butyl acrylate, t-butyl acrylate) and/or derivatives (such as anhydrides and imides) of unsaturated carboxylic acids (for example maleic anhydride and N-phenyl maleinimide).

Preferred monomers A.1.1 are selected from at least one of the monomers styrene, α-methyl styrene and methyl methacrylate; preferred monomers A.1.2 are selected from at least one of the monomers acrylonitrile, maleic anhydride and methyl methacrylate.

Particularly preferred monomers are A.1.1 styrene and A.1.2 acrylonitrile.

Suitable graft bases A.2 are for example diene rubbers, EP(D)M rubbers, in other words those based on ethylene/propylene and optionally diene, acrylate, polyurethane, silicone, chloroprene and ethylene/vinyl acetate rubbers.

Suitable acrylate rubbers according to A.2 are preferably polymers of acrylic acid alkyl esters, optionally with up to 40 wt. %, relative to A.2, of other polymerizable, ethylenically unsaturated monomers. The preferred polymerizable acrylic acid esters include $C_1$–$C_8$ alkyl esters, for example methyl, ethyl, butyl, n-octyl and 2-ethylhexyl ester; haloalkyl esters, preferably halogen $C_1$–$C_8$ alkyl esters, such as chloroethyl acrylate and mixtures of these monomers.

Monomers having more than one polymerizable double bond can be copolymerized for crosslinking. Preferred examples of crosslinking monomers are esters of unsaturated monocarboxylic acids having 3 to 8 C atoms and unsaturated monohydric alcohols having 3 to 12 C atoms, or saturated polyols having 2 to 4 OH groups and 2 to 20 C atoms, such as ethylene glycol dimethacrylate, allyl methacrylate; polyunsaturated heterocyclic compounds, such as trivinyl and triallyl cyanurate; polyfunctional vinyl compounds, such as divinyl and trivinyl benzenes; but also triallyl phosphate and diallyl phthalate.

Preferred crosslinking monomers are allyl methacrylate, ethylene glycol dimethacrylate, diallyl phthalate and heterocyclic compounds displaying at least three ethylenically unsaturated groups.

Particularly preferred crosslinking monomers are the cyclic monomers triallyl cyanurate, triallyl isocyanurate, triacryloyl hexahydro-s-triazine, triallyl benzenes. The quantity of crosslinked monomers is preferably 0.02 to 5, in particular 0.05 to 2 wt. %, relative to the graft base A.2.

In the case of cyclic crosslinking monomers having at least three ethylenically unsaturated groups it is advantageous to limit their quantity to below 1 wt. % relative to the graft base A.2.

Preferred "other" polymerizable, ethylen ically unsaturated monomers, which may optionally be used in addition to the acrylic acid esters to produce the graft base A.2, are for example acrylonitrile, styrene, α-methyl styrene, acrylamides, vinyl $C_1$–$C_6$ alkyl ethers, methyl methacrylate, butadiene. Preferred acrylate rubbers as graft base A.2 are emulsion polymers displaying a gel content of at least 60 wt. %.

Other suitable graft bases according to A.2 are silicone rubbers with graft-active sites, such as those described in DE-A 37 04 657, DE-A 37 04 655, DE-A 36 31 540 and DE-A 36 31 539.

Preferred graft bases A.2 are diene rubbers (based for example on butadiene, isoprene, etc.) or mixtures of diene rubbers and copolymers of diene rubbers or mixtures thereof with other copolymerizable monomers (according to A.1.1 and A.1.2, for example), with the proviso that the glass transition temperature of component A.2 is below <10° C., preferably <0° C., particularly preferably <−10° C. Pure polybutadiene rubber is particularly preferred. The gel content of graft base A.2 is at least 30 wt. %, preferably at least 40 wt. % (measured in toluene).

The gel content of graft base A.2 is determined at 25° C. in a suitable solvent (M. Hoffmann, H. Krömer, R. Kuhn, Polymeranalytik I und II, Georg Thieme-Verlag, Stuttgart 1977).

The graft base A.2 generally has an average particle size ($d_{50}$ value) of 0.05 to 10 μm, preferably 0.1 to 5 μm, particularly preferably 0.2 to 1 μm.

The median particle size $d_{50}$ is the diameter above and below which respectively 50 wt. % of the particles lie. It may be determined by ultracentrifuge measurement (W. Scholtan, H. Lange, Kolloid, Z. und Z. Polymere 250 (1972), 782–1796).

The graft polymers are produced by radical polymerization, for example by emulsion, suspension, solution or bulk polymerization, preferably by emulsion or suspension polymerization.

Conventional anionic emulsifiers such as alkyl sulfates, alkyl sulfonates, aralkyl sulfonates, soaps of saturated or unsaturated fatty acids and of alkaline disproportionated or hydrogenated abietic or tall oil acids may be used as emulsifiers in emulsion or suspension polymerizations. Emulsifiers containing carboxyl groups (e.g. salts of $C_{10}$–$C_{18}$ fatty acids, disproportionated abietic acid, emulsifiers according to DE-A 36 39 904 and DE-A 39 13 509) may also be used.

Molecular weight regulators may additionally be used in the graft polymerization, preferably in quantities of 0.01 to 2 wt. %, particularly preferably in quantities of 0.05 to 1 wt. % (relative in each case to the total quantity of monomer in the graft polymerization stage). Suitable molecular weight regulators are for example alkyl mercaptans such as n-dodecyl mercaptan, t-dodecyl mercaptan; dimeric α-methyl styrene; terpinolene.

Suitable examples of initiators include inorganic and organic peroxides, e.g. $H_2O_2$, di-tert.-butyl peroxide, cumene hydroperoxide, dicyclohexyl percarbonate, tert.-butyl hydroperoxide, p-menthane hydroperoxide, azo initiators such as azobisisobutyronitrile, inorganic persalts such as ammonium, sodium or potassium persulfate, potassium perphosphate, sodium perborate and redox systems.

Redox systems include an organic oxidizing agent and a reducing agent, whereby heavy metal ions may additionally be present in the reaction medium (see Houben-Weyl, Methoden der Organischen Chemie, Volume 14/1, p. 263–297).

The polymerization temperature is generally 25° C. to 160° C., preferably 40° C. to 90° C. The process can take place under conventional temperature control, e.g. isothermically; preferably, however, the graft polymerization is performed in such a way that the temperature difference between the start and end of the reaction is at least 10° C., preferably at least 15° C. and particularly preferably at least 20° C.

Since it is known that the graft monomers are not necessarily completely grafted onto the graft base during the graft reaction, the term graft polymers A according to the invention also refers to products which are obtained by (co) polymerization of the graft monomers in the presence of the graft base and which accumulate during processing.

The process according to the invention may particularly preferably be used for the controlled production of ABS by grafting of polybutadiene, whereby a known amount of polybutadiene $M_{PB}$ is placed in a reactor in the form of an emulsion, grafting is started at time t=0 and performed by known means by continuous addition and polymerization of the monomers styrene and acrylonitrile, and the Raman spectra I($\upsilon$) are recorded at short intervals, preferably in the range 4000 to 100 cm$^{-1}$ (Stokes range), otherwise in the range −4000 to 4000 cm$^{-1}$ (anti-Stokes and Stokes range). In contrast to the teaching from WO 00/49 395, polybutadiene is used according to the invention as the internal standard for interpreting the Raman spectra.

In the case of an ABS graft reaction the spectral range 1550–1700 cm$^{-1}$ is particularly interesting, since the components involved display characteristic Raman peaks there:

| | | |
|---|---|---|
| 1667 cm$^{-1}$: | 1,4-trans-polybutadiene | C=C valence vibration |
| 1654 cm$^{-1}$: | 1,4-cis-polybutadiene | C=C valence vibration |
| 1641 cm$^{-1}$: | 1,2-vinyl polybutadiene/butadiene | C=C valence vibration |
| 1632 cm$^{-1}$: | styrene (monomer) | C=C valence vibration |
| 1609 cm$^{-1}$: | acrylonitrile (monomer) | C=C valence vibration |
| 1602 cm$^{-1}$: | styrene/polystyrene | aromatics vibration |
| 1583 cm$^{-1}$: | polystyrene | aromatics vibration |

For example, in butadiene emulsion polymerization the butadiene/polybutadiene ratio can be determined very accurately online once the monomer droplets have disappeared. If the amount of butadiene added is known, the conversion is therefore also known.

In the case of the ABS graft reaction with a known polybutadiene concentration, Raman spectroscopy may be used to detect online the concentrations of the monomers acrylonitrile and styrene, the polymer content, the ABS copolymer contents and the conversion.

Graft polymers with reproducible properties may be produced with the aid of the process according to the invention, since keeping the monomer ratios constant ensures that a graft polymer having a constant composition is produced. The end point of the reaction may optionally also be detected with the aid of the present invention.

EXAMPLES

The invention is clarified below by means of examples.

Embodiment Examples

Example 1

Production of ABS 1.1 Polymerization

| | | |
|---|---|---|
| Fraction A: | Polybutadiene latex with 30% solids content, having a particle size between 200 and 400 nm | 21570 g |
| | Surfactant solution, 7.5% in water | 438.1 g |
| Fraction B: | Potassium persulfate | 54.8 g |
| | Deionised water | 2190.5 g |
| Fraction C: | Styrene, technical | 3105 g |
| | Acrylonitrile, technical | 1495 g |
| | tert.-Dodecyl mercaptan | 16.6 g |
| Fraction D: | Surfactant solution, 7.5% in water | 1752.4 g |

The reaction vessel including the loop for sample measurement is rinsed with nitrogen. Fraction A is then introduced and heated up to 62° C. after switching on the reactor. As soon as the temperature reaches 62° C. fraction B is added within 5 minutes. Fractions C and D are then added in 6 hours, whereby the temperature is held at 62° C. The temperature is then raised to 70° C. The reaction mixture remains at this temperature for 3 hours and is then cooled to 25° C., the reactor is opened and the product removed.

1.2 Analysis of the Polymerization

The Raman spectra are recorded with an RFS 100 FT Raman spectrometer supplied by Bruker. The Nd:YAG laser inside it is operated at a power of 1.2 watts. The spectrometer is fitted with a probe coupled to an optical fibre.

Figure 2:
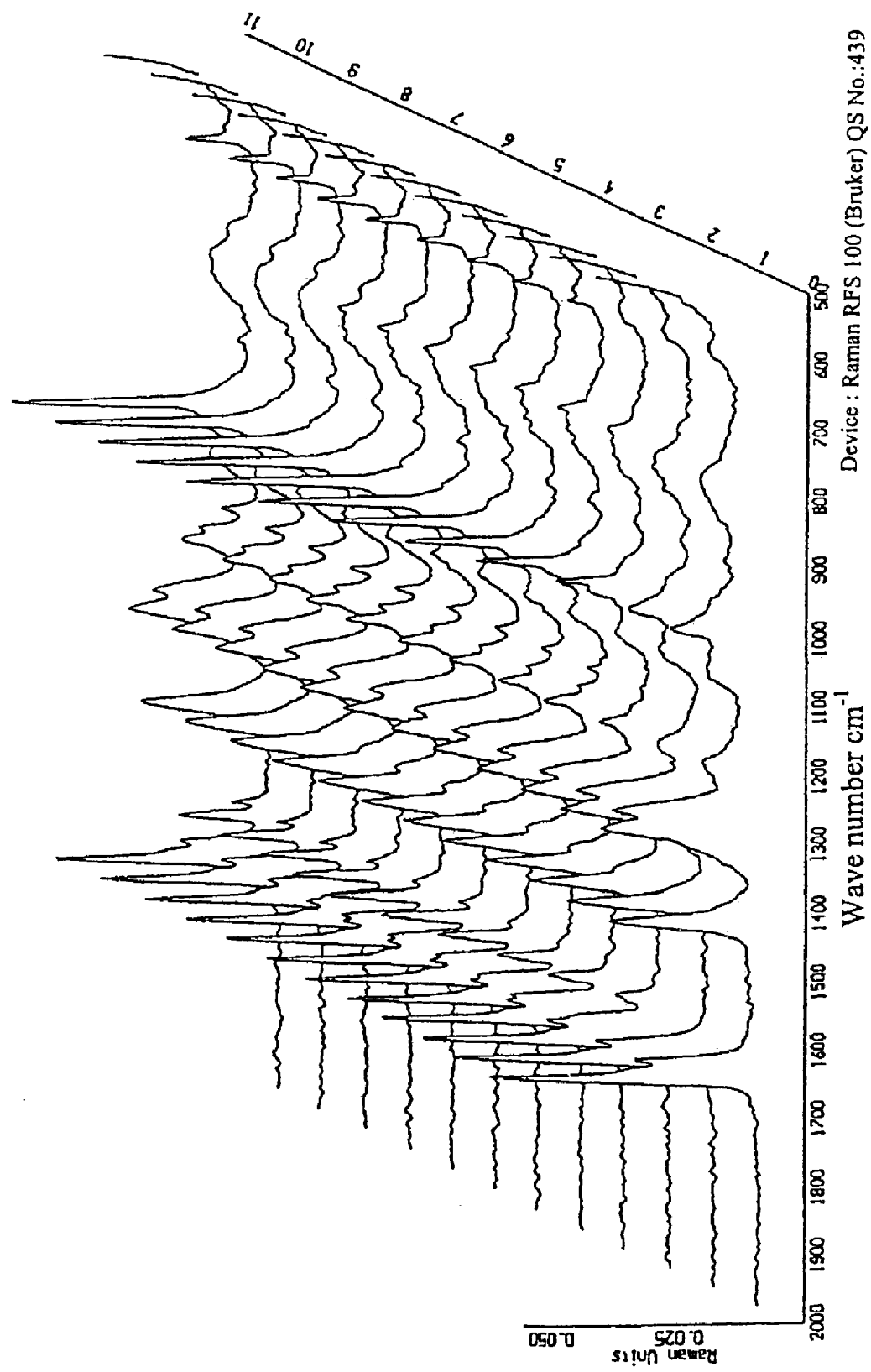

The Raman spectra are recorded every 5 minutes at a resolution of 4 cm$^{-1}$. They are stored in a computer and analyzed by the method described below. The spectra obtained are reproduced in FIG. 2.

The Raman spectra $I_{PB}(\upsilon)$ of polybutadiene (PB), $I_{PS}(\upsilon)$ of polystyrene (PS), $I_{PAN}(\upsilon)$ of polyacrylonitrile (PAN), $I_{STY}(\upsilon)$ of styrene (STY) and $I_{ACN}(\upsilon)$ of acrylonitrile (ACN) that have previously been measured and stored in digitised form in an EDP unit and the current spectrum $I(\upsilon)$ of the reactor content at $\upsilon_{min}$=750 cm$^{-1}$ and $\upsilon_{max}$=1800 cm$^{-1}$ are used to calculate the factors $f_i$ (weighted subtraction) using the condition:

$$\sum_{\upsilon_{min}}^{\upsilon_{max}} \{I(\upsilon) + [f_{PB} * I_{PB}(\upsilon) + f_{PS} * I_{PS}(\upsilon) + f_{PAN} * I_{PAN}(\upsilon) + f_{STY} * I_{STY}(\upsilon) + f_{ACN} * I_{ACN}(\upsilon) + f_k]\}^2 = \text{minimum}$$

whereby the addition is performed across all data points of the spectra $I_i(\upsilon)$ which are digitized in the same form. From these the quotients $Q_{PS} = f_{PS}/f_{PB}$ $Q_{PAN} = f_{PAN}/f_{PB}$ $Q_{STY} = f_{STY}/f_{PB}$ $Q_{ACN} = f_{ACN}/f_{PB}$ and, using the calibration factors K, the proportions W of:

polystyrene to polybutadiene: $W_{PS} = K_{PS} * Q_{PS}$ polyacrylonitrile to polybutadiene: $W_{PAN} = K_{PAN} * Q_{PAN}$ styrene to polybutadiene: $W_{STY} = K_{STY} * Q_{STY}$ acrylonitrile to polybutadiene: $W_{ACN} = K_{ACN} * Q_{ACN}$ are calculated, from which using:

$M_{PS} = W_{PS} * M_{PB}$ $M_{PAN} = W_{PAN} * M_{PB}$ $$M_{STY} = W_{STY} * M_{PB}$$

$$M_{ACN} = W_{ACN} * M_{PB}$$

the absolute quantities of polystyrene $M_{PS}$, polyacrylonitrile $M_{PAN}$, styrene $M_{STY}$ and acrylonitrile $M_{ACN}$ in the reactor are calculated.

The factors $K_{PS}$, $K_{PAN}$, $K_{STY}$ and $K_{ACN}$ are first determined in a calibration step, whereby the Raman spectra $I_K(\upsilon)$ of mixtures with known proportions are recorded and the factors $f_i$ are calculated using the condition:

$$\sum_{\upsilon_{min}}^{\upsilon_{max}} \{I_k(\upsilon) - [f_{PB} * I_{PB}(\upsilon) + f_{PS} * I_{PS}(\upsilon) + f_{PAN} * I_{PAN}(\upsilon) + f_{STY} * I_{STY}(\upsilon) + f_{ACN} * I_{ACN}(\upsilon) + f_k]\}^2 = \text{minimum}$$

from which are calculated the quotients $$Q_{PS} = f_{PS}/f_{PB}$$

$$Q_{PAN} = f_{PAN}/f_{PB}$$

$$Q_{STY} = f_{STY}/f_{PB}$$

$$Q_{ACN} = f_{ACN}/f_{PB}$$

the parts by weight W are calculated with the known quantities M:

$$W_{PS} = M_{PS}/M_{PB}$$

$$W_{PAN} = M_{PAN}/M_{PB}$$

$$W_{STY} = M_{STY}/M_{PB}$$

$$W_{ACN} = M_{ACN}/M_{PB}$$

and the calibration factors K are calculated from the following equations:

$$K_{PS} = W_{PS}/Q_{PS}$$

$$K_{PAN} = W_{PAN}/Q_{PAN}$$

$$K_{STY} = W_{STY}/Q_{STY}$$

$$K_{ACN} = W_{ACN}/Q_{ACN}$$

1.3 Results

The Raman spectra recorded during the graft reaction according to the graft formulation are interpreted on the basis of the calibration described. Starting from the known starting amount of polybutadiene, the absolute quantities of acrylonitrile, styrene, polyacrylonitrile and polystyrene are determined from the Raman spectra. In this way the content of polymer is also known.

The instantaneous conversion U relative to the added monomers, determined gravimetrically by offline measurement $$U = (W_{PS} + W_{PAN})/(W_{PS} + W_{PAN} + W_{STY} + W_{ACN})$$

is compared with the conversion determined using Raman spectroscopy. A satisfactory agreement is found.

Figure 3:
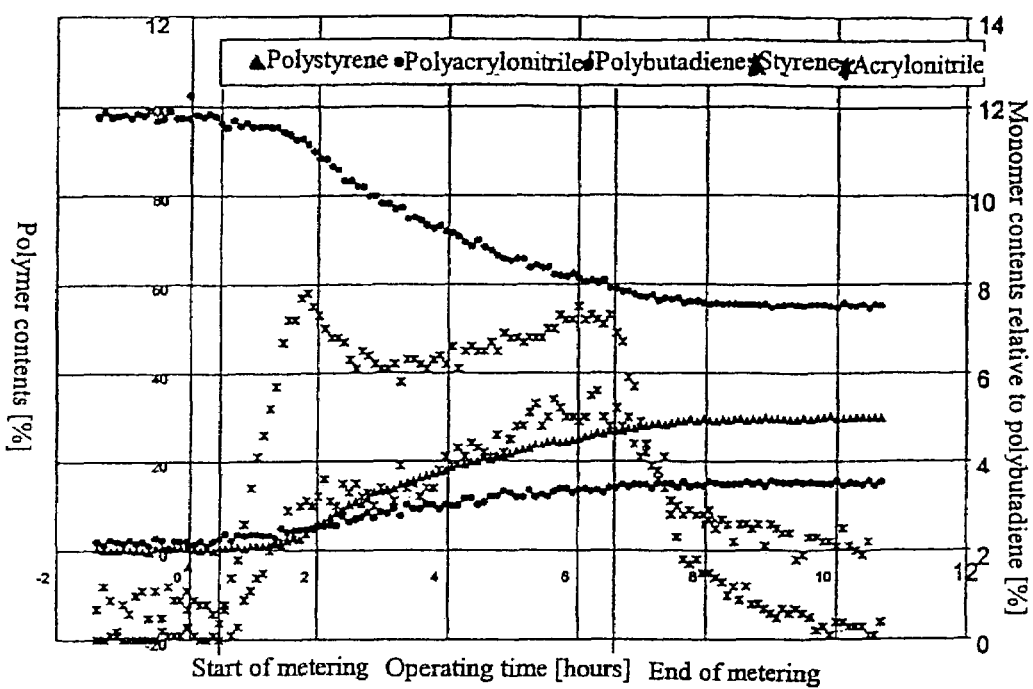

The concentrations of the reagents are accurately obtained from the Raman spectra obtained, as illustrated in FIG. 3:

| | |
|---|---|
| Abscissas: | Operating time, corrected by the time offset due to measurement in the loop. |
| Left-hand ordinates: | Polymer concentrations (polybutadiene, polymerized styrene in poly(styrene-co-acrylonitrile), polymerized acrylonitrile in poly(styrene-co-acrylonitrile)), which add up to 100 wt. %; |
| Right-hand ordinates: | Monomer concentrations (styrene-acrylonitrile) relative to the starting mass of polybutadiene |

Examples 2 to 4

These experiments are exact reproductions of Example 1 and can be interpreted in the same way.

The absolute quantities of polystyrene $M_{PS}$, polyacrylonitrile $M_{PAN}$, styrene $M_{STY}$ and acrylonitrile $M_{ACN}$ in the reactor are calculated, these are compared with the required quantities after a time $\Delta t$ from the start of polymerization and the current quantities are adjusted to the required quantities for the reaction at time $t_0 + \Delta t$ by varying the quantities of styrene and acrylonitrile that are added or by increasing or reducing the polymerization rates.

Figure 4:
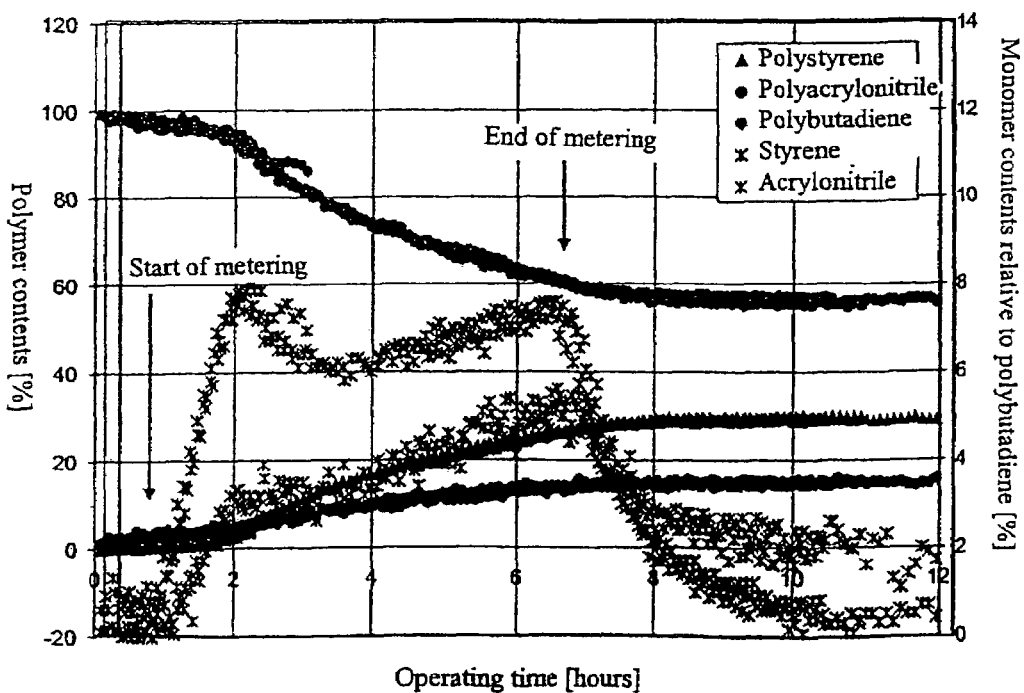

The results from all four examples are set out one below the other with labels in FIG. 4. It can be seen that the deviations are slight and the scattering of the measurement results is very small.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method using Raman Spectra for determining the progress of a graft polymerization reaction comprising:
    (a) measuring at the beginning of the reaction and at a plurality of time intervals in the course of the reaction, continuously and on-site, the Raman spectrum in the wave number range of 100 to 4000 cm$^{-1}$ of one or more of monomers and/or polymers entailed in the reaction and a graft base, which is used as an internal standard; and
    (b) calculating the change in concentration of the monomers and polymers from the spectra in consideration of the internal standard.

2. The method of claim 1 wherein the quantities of the monomers and polymers are calculated from the current Raman spectrum during the course of the reaction by weighted subtraction of the spectra of the monomers and the polymers.

3. The method of claim 1, wherein said graft base is introduced in its entirely before the start of a batchwise reaction.

4. The method of claim 1 wherein the Raman spectra are measured in the wave number range of 500 to 2500 cm$^{-1}$.

5. The method of claim 1 wherein the Raman spectra are measured in the wave number range of 750 to 1800 cm$^{-1}$.

6. A process for the preparation of graft polymers comprising
    a) adding at least one of the reactants in a continuous and/or discontinuous manner, b) obtaining at a plurality of time in the course of the reaction the concentrations of the monomers and/or polymers using the method of claim 1, c) comprising said concentrations with the required concentrations at the time and d) adjusting the current quantities to the required quantities at the following time interval by varying the quantities of at least one of the monomers that are added or by increasing or decreasing the polymerization rates.

7. The method of claim 6 wherein the graft polymerization reaction entails grafting a mixture containing A.1 5 to 95 wt. % of at least one vinyl monomer onto A.2 95 to 5 wt. % of one or more graft bases having glass transition temperatures <10° C., the percent being relative to the total weight of A.1 and A2.

8. The method of claim 6 wherein A.1 is a mixture of

A.1.1 50 to 99 parts by weight of at least one compound selected from the group consisting of styrene, α-methyl styrene, p-methyl styrene, p-chlorostyrene and methacrylic acid ($C_1$–$C_8$) alkyl esters and A.1.2 1 to 50 parts by weight of at least one compound selected from the group consisting of acrylonitrile, methacrylonitrile, (meth)acrylic acid ($C_1$–$C_8$) alkyl esters and derivatives of unsaturated carboxylic acids.

9. The method of claim 6 wherein A.2 is selected from the group consisting of diene rubbers, EP(D)M rubbers, acrylate, polyurethane, silicone, chloroprene end ethylene/vinyl acetate rubber.

10. The method of claim 6 wherein the reaction is initiated with at least one inorganic or organic peroxide.

11. The method of claim 6 wherein the reaction is initiated by a system that contains an organic hydroperoxide and ascorbic acid.

* * * * *